(12) United States Patent  (10) Patent No.: US 7,572,823 B2
Conte et al.  (45) Date of Patent: Aug. 11, 2009

(54) HETEROARYL CARBOXAMIDE COMPOUNDS

(75) Inventors: Aurelia Conte, Basel (CH); Holger Kuehne, Grenzach-Wyhlen (DE); Thomas Luebbers, Loerrach (DE); Patrizio Mattei, Riehen (CH); Cyrille Maugeais, Mulhouse (FR); Werner Mueller, Aesch BL (CH); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 373 days.

(21) Appl. No.: 11/698,677

(22) Filed: Jan. 26, 2007

(65) Prior Publication Data

US 2007/0185182 A1 Aug. 9, 2007

(30) Foreign Application Priority Data

Feb. 7, 2006 (EP) .................................. 06101377

(51) Int. Cl.
*A61K 31/416* (2006.01)
*C07D 209/30* (2006.01)
(52) U.S. Cl. .................... 514/406; 514/419; 548/360.1; 548/503
(58) Field of Classification Search ........................ None
See application file for complete search history.

(56) References Cited

FOREIGN PATENT DOCUMENTS

EP 1 533 292 B1 2/2007

WO WO 2006/013048 A1 2/2006

OTHER PUBLICATIONS

Le Goff et al., Pharmacology & Therapeutics, 101, pp. 17-38 (2004).
Okamoto et al., Nature, 406, pp. 203-207 (2000).
Stanetty, P., et al., Archiv Der Pharmazie, vol. 325, pp. 433-437 (1992), XP002427831.
Tacke, R., et al., Endeavour, vol. 10, No. 4, pp. 191-197 (1986), XP008002622.
Tacke, R., et al., *Chapter 18: Bioorganosilicon Chemistry*, The Chemistry of Organic Silicon Compounds, pp. 1158-1182 (1989), XP007902422.
Barcza, S., *Chapter 13: The value and new directions of silicon chemistry for obtaining bioactive compounds*, Organosilicon Chemistry (1987), XP007902424.

*Primary Examiner*—Kamal A Saeed
(74) *Attorney, Agent, or Firm*—George W. Johnston; Dennis P. Tramaloni; Brian C. Remy

(57) ABSTRACT

Compounds of formula I

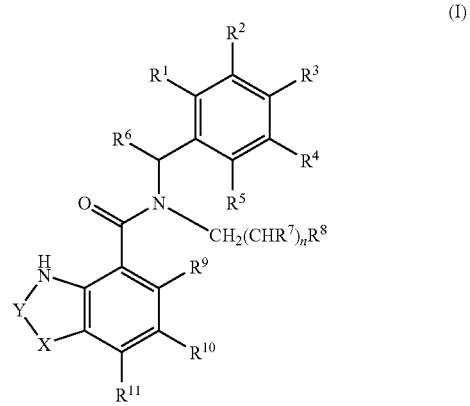

their manufacture, pharmaceutical compositions containing them and their use as medicaments.

16 Claims, No Drawings

HETEROARYL CARBOXAMIDE COMPOUNDS

PRIORITY TO RELATED APPLICATIONS

This application claims the benefit of European Application No. 06101377.7, filed Feb. 7, 2006, which is hereby incorporated by reference in its entirety.

The present invention is concerned with novel 1H-indole-7-carboxamido, 1H-indazole-7-carboxamido or 1H-indoline-7-carboxamido derivatives, their manufacture, pharmaceutical compositions containing them and their use as medicaments.

In a first aspect the present invention relates to a compound of formula I

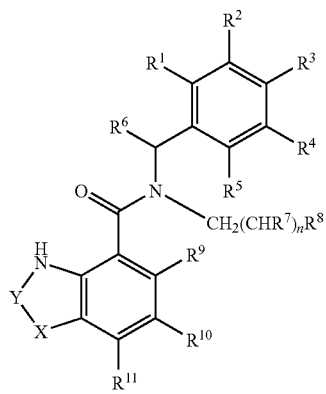

(I)

wherein

—X—Y— is —$CR^a$=$CR^c$— or —$CR^a$=N— or —$CR^aR^b$—$CR^cR^d$—, wherein $R^a$, $R^b$, $R^c$ and $R^d$ are independently from each other selected from the group consisting of hydrogen and $C_1$-$C_8$alkyl;

$R^1$, $R^2$, $R^4$ and $R^5$ are independently from each other selected from the group consisting of hydrogen, $C_1$-$C_8$alkyl, $C_1$-$C_8$alkoxy, halogen and halogen-$C_1$-$C_8$alkyl;

$R^3$ is $Si(C_1$-$C_6alkyl)_3$;

$R^6$ is selected from the group consisting of hydrogen and $C_1$-$C_8$alkyl;

$R^7$ is selected from the group consisting of hydrogen, $C_1$-$C_8$alkyl, hydroxy and halogen;

$R^8$ is selected from the group consisting of $C_1$-$C_8$alkyl, $C_2$-$C_8$alkenyl, halogen-$C_1$-$C_8$alkyl, heterocyclyl, heteroaryl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$OR^{12}$, wherein $R^{12}$ is $C_1$-$C_8$alkyl or phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$NR^{13}R^{14}$, wherein $R^{13}$ and $R^{14}$ independently from each other are selected from hydrogen, $C_1$-$C_8$alkyl, and phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, and —C(O)—$OR^{15}$, wherein $R^{15}$ is hydrogen or $C_1$-$C_8$alkyl;

$R^9$, $R^{10}$ and $R^{11}$ independently from each other are selected from the group consisting of hydrogen, $C_1$-$C_8$alkyl, cycloalkyl, $C_1$-$C_8$alkoxy, halogen-$C_1$-$C_8$alkyl, and halogen;

n is 1, 2 or 3;

and all pharmaceutically acceptable salts thereof.

In another embodiment the present invention relates to a compound of the formula I wherein —X—Y— is —$CR^a$=$CR^c$— or —$CR^a$=N— or —$CR^aR^b$—$CR^cR^d$—, wherein $R^a$, $R^b$, $R^c$ and $R^d$ are independently from each other selected from the group consisting of hydrogen and $C_1$-$C_8$alkyl;

$R^1$, $R^2$, $R^4$ and $R^5$ are independently from each other selected from the group consisting of hydrogen, $C_1$-$C_8$alkyl, $C_1$-$C_8$alkoxy, halogen and halogen-$C_1$-$C_8$alkyl;

$R^3$ is $Si(C_1$-$C_6alkyl)_3$;

$R^6$ is selected from the group consisting of hydrogen and $C_1$-$C_8$alkyl;

$R^7$ is selected from the group consisting of hydrogen, $C_1$-$C_8$alkyl, hydroxy and halogen;

$R^8$ is selected from the group consisting of $C_1$-$C_8$alkyl, $C_2$-$C_8$alkenyl, halogen-$C_1$-$C_8$alkyl, heterocyclyl, heteroaryl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$OR^{12}$, wherein $R^{12}$ is $C_1$-$C_8$alkyl or phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$NR^{13}R^{14}$, wherein $R^{13}$ and $R^{14}$ independently from each other are selected from hydrogen, $C_1$-$C_8$alkyl, and phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, and —C(O)—$OR^{15}$, wherein $R^{15}$ is hydrogen or $C_1$-$C_8$alkyl;

$R^9$, $R^{10}$ and $R^{11}$ independently from each other are selected from the group consisting of hydrogen, $C_1$-$C_8$alkyl, $C_3$-$C_8$cycloalkyl, $C_1$-$C_8$alkoxy, halogen-$C_1$-$C_8$alkyl, and halogen;

n is 1, 2 or 3;

and all pharmaceutically acceptable salts thereof.

Unless otherwise indicated the following definitions are set forth to illustrate and define the meaning and scope of the various terms used to describe the invention herein.

The term "$C_1$-$C_8$-alkyl", alone or in combination, signifies a straight-chain or branched-chain alkyl group with 1 to 8 carbon atoms, e.g. a straight or branched-chain alkyl group with 1 to 6 carbon atoms, e.g. a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, e.g. methyl, ethyl and tert.-butyl.

The term "$C_{2-8}$-alkenyl", alone or in combination, means a straight-chain or branched hydrocarbon radical comprising an olefinic bond and up to 8, e.g., up to 6, e.g., up to 4 carbon atoms. Examples of alkenyl groups are ethenyl, 1-propenyl, 2-propenyl, isopropenyl, 1-butenyl, 2-butenyl, 3-butenyl and isobutenyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl, e.g. cyclopropyl, cyclobutyl and cyclopentyl.

The term alkoxy refers to the group R'—O—, wherein R' is $C_1$-$C_8$alkyl and the term $C_1$-$C_8$alkyl has the previously given significance. Examples of $C_1$-$C_8$alkoxy groups are e.g. methoxy, ethoxy, n-propoxy, isopropoxy, n-butoxy, isobutoxy, sec. butoxy and tert.butoxy, e.g. methoxy and ethoxy, e.g. methoxy.

The term "$C_{1-8}$-alkoxy-$C_{1-8}$-alkyl" refers to $C_1$-$C_8$alkyl groups as defined above wherein at least one of the hydrogen atoms of the $C_1$-$C_8$alkyl groups is replaced by an alkoxy group, e.g. methoxy or ethoxy. Examples of $C_1$-$C_8$alkoxy-$C_1$-$C_8$alkyl groups include 2-methoxyethyl, 3-methoxypropyl and 1-methoxy-1-methyl-ethyl.

The term "halogen" refers to fluorine, chlorine, bromine and iodine.

The term "halogen-$C_1$-$C_8$alkyl" refers to $C_1$-$C_8$alkyl groups as defined above wherein at least one of the hydrogen atoms of the $C_1$-$C_8$alkyl group is replaced by a halogen atom, e.g. fluoro or chloro. Examples of halogenated $C_1$-$C_8$alkyl groups include trifluoromethyl, difluoromethyl, fluoromethyl and chlorodifluoromethyl.

The term "halogen-$C_1$-$C_8$alkoxy" refers to $C_1$-$C_8$alkoxy groups as defined above wherein at least one of the hydrogen atoms of the $C_1$-$C_8$alkoxy group is replaced by a halogen atom, e.g. fluoro or chloro. Examples of halogenated $C_1$-$C_8$alkyl groups include trifluoromethoxy, difluoromethoxy, fluoromethoxy and chlorodifluoromethoxy.

The term "$C_1$-$C_8$alkoxy-halogen-$C_1$-$C_8$alkyl" refers to halogen-$C_1$-$C_8$alkyl groups as defined above wherein at least one of the hydrogen atoms of the halogen-$C_1$-$C_8$alkyl group is replaced by an alkoxy group. An example of a $C_1$-$C_8$alkoxy-halogen-$C_1$-$C_8$alkyl group is 2,2,2-trifluoro-1-methoxy-1-trifluoromethyl-ethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl, e.g. furyl, thienyl, thiazolyl and pyridyl.

The term "heterocyclyl" refers to a saturated or partly unsaturated 5- or 6-membered ring comprising one, two or three atoms selected from nitrogen, oxygen and sulphur. Examples of heterocyclyl include piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, tetrahydrothiopyranyl and thiamorpholinyl, e.g. tetrahydrothiopyranyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid or phosphoric acid, e.g. hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In one embodiment the present invention provides a compound of formula I wherein —X—Y— signifies —CR$^a$=CR$^c$— and R$^a$ and R$^c$ are independently from each other selected from the group consisting of hydrogen and $C_1$-$C_8$alkyl. In another embodiment the present invention provides a compound of formula I wherein —X—Y— signifies —CR$^a$=CR$^c$— and R$^a$ and R$^c$ are hydrogen.

In one embodiment the present invention provides compounds of formula I having the formula

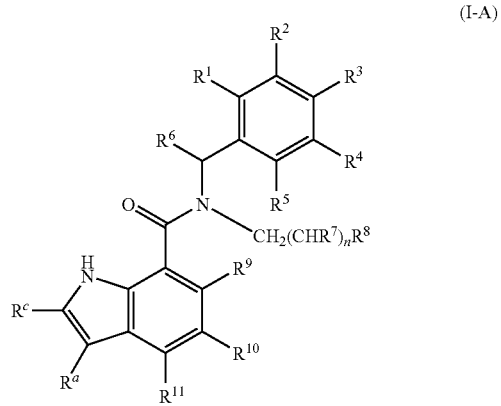

(I-A)

wherein

R$^a$ and R$^c$ are independently from each other selected from the group consisting of hydrogen and $C_1$-$C_8$alkyl;

R$^1$, R$^2$, R$^4$ and R$^5$ are independently from each other selected from the group consisting of hydrogen, $C_1$-$C_8$alkyl, $C_1$-$C_8$alkoxy, halogen and halogen-$C_1$-$C_8$alkyl;

R$^3$ is Si($C_1$-$C_6$alkyl)$_3$;

R$^6$ is selected from the group consisting of hydrogen and $C_1$-$C_8$alkyl;

R$^7$ is selected from the group consisting of hydrogen, $C_1$-$C_8$alkyl, hydroxy and halogen;

$R^8$ is selected from the group consisting of $C_1$-$C_8$alkyl, $C_2$-$C_8$alkenyl, halogen-$C_1$-$C_8$alkyl, heterocyclyl, heteroaryl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$OR^{12}$, wherein $R^{12}$ is $C_1$-$C_8$alkyl or phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$NR^{13}R^{14}$, wherein $R^{13}$ and $R^{14}$ independently from each other are selected from hydrogen, $C_1$-$C_8$alkyl, and phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, and —C(O)—$OR^{15}$, wherein $R^{15}$ is hydrogen or $C_1$-$C_8$alkyl;

$R^9$, $R^{10}$ and $R^{11}$ independently from each other are selected from the group consisting of hydrogen, $C_1$-$C_8$alkyl, $C_3$-$C_8$cycloalkyl, $C_1$-$C_8$alkoxy, halogen-$C_1$-$C_8$alkyl, and halogen;

n is 1, 2 or 3;

and all pharmaceutically acceptable salts thereof.

In another embodiment the invention further provides compounds of formula I, wherein —X—Y— is —$CR^a$=N— and $R^a$ is hydrogen or $C_1$-$C_8$alkyl; thus meaning compounds of formula I having the formula

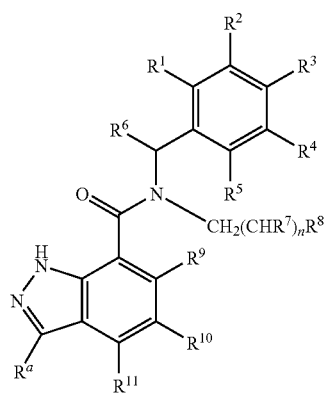

(I-B)

wherein
$R^a$ is hydrogen and $C_1$-$C_8$alkyl;
$R^1$, $R^2$, $R^4$ and $R^5$ are independently from each other selected from the group consisting of hydrogen, $C_1$-$C_8$alkyl, $C_1$-$C_8$alkoxy, halogen and halogen-$C_1$-$C_8$alkyl;
$R^3$ is Si($C_1$-$C_6$alkyl)$_3$;
$R^6$ is selected from the group consisting of hydrogen and $C_1$-$C_8$alkyl;
$R^7$ is selected from the group consisting of hydrogen, $C_1$-$C_8$alkyl, hydroxy and halogen;
$R^8$ is selected from the group consisting of $C_1$-$C_8$alkyl, $C_2$-$C_8$alkenyl, halogen-$C_1$-$C_8$alkyl, heterocyclyl, heteroaryl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$OR^{12}$, wherein $R^{12}$ is $C_1$-$C_8$alkyl or phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$NR^{13}R^{14}$, wherein $R^{13}$ and $R^{14}$ independently from each other are selected from hydrogen, $C_1$-$C_8$alkyl, and phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, and —C(O)—$OR^{15}$, wherein $R^{15}$ is hydrogen or $C_1$-$C_8$alkyl;

$R^9$, $R^{10}$ and $R^{11}$ independently from each other are selected from the group consisting of hydrogen, $C_1$-$C_8$alkyl, $C_3$-$C_8$cycloalkyl, $C_1$-$C_8$alkoxy, halogen-$C_1$-$C_8$alkyl, and halogen;

n is 1, 2 or 3;

and all pharmaceutically acceptable salts thereof.

In one embodiment the present invention provides a compound of formula I-B wherein $R^a$ is hydrogen.

Furthermore, the invention relates to compounds of formula I, wherein —X—Y— signifies —$CR^aR^b$—$CR^cR^d$— and $R^a$, $R^b$, $R^c$ and $R^d$ are independently from each other selected from the group consisting of hydrogen and $C_1$-$C_8$alkyl; thus meaning compounds of formula I having the formula

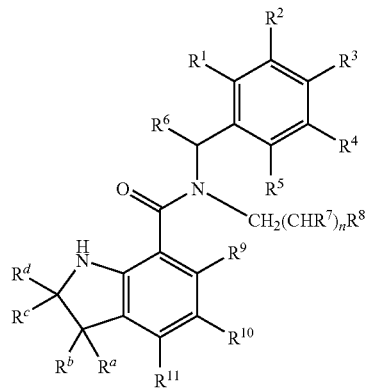

(I-C)

wherein
$R^a$, $R^b$, $R^c$ and $R^d$ are independently from each other selected from the group consisting of hydrogen and $C_1$-$C_8$alkyl;
$R^1$, $R^2$, $R^4$ and $R^5$ are independently from each other selected from the group consisting of hydrogen, $C_1$-$C_8$alkyl, $C_1$-$C_8$alkoxy, halogen and halogen-$C_1$-$C_8$alkyl;
$R^3$ is Si($C_1$-$C_6$alkyl)$_3$;
$R^6$ is selected from the group consisting of hydrogen and $C_1$-$C_8$alkyl;
$R^7$ is selected from the group consisting of hydrogen, $C_1$-$C_8$alkyl, hydroxy and halogen;
$R^8$ is selected from the group consisting of $C_1$-$C_8$alkyl, $C_2$-$C_8$alkenyl, halogen-$C_1$-$C_8$alkyl, heterocyclyl, heteroaryl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$OR^{12}$, wherein $R^{12}$ is $C_1$-$C_8$alkyl or phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, —$NR^{13}R^{14}$, wherein $R^{13}$ and $R^{14}$ independently from each other are selected from hydrogen, $C_1$-$C_8$alkyl, and phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen, and —C(O)—$OR^{15}$, wherein $R^{15}$ is hydrogen or $C_1$-$C_8$alkyl;

$R^9$, $R^{10}$ and $R^{11}$ independently from each other are selected from the group consisting of hydrogen, $C_1$-$C_8$alkyl, cycloalkyl, $C_1$-$C_8$alkoxy, halogen-$C_1$-$C_8$alkyl, and halogen;

n is 1, 2 or 3;

and all pharmaceutically acceptable salts thereof.

In one embodiment the present invention provides compounds of formula I-C, wherein $R^a$, $R^b$, $R^c$ and $R^d$ are hydrogen.

In another embodiment the present invention provides a compound of formula I wherein $R^1$, $R^2$, $R^4$ and $R^5$ are hydrogen.

In still another embodiment the present invention provides compounds of formula I wherein $R^1$ is $C_1$-$C_8$alkoxy or halogen and $R^2$, $R^4$ and $R^5$ are hydrogen. In still another embodiment the present invention provides compounds of formula I, wherein $R^2$ is halogen and $R^1$, $R^4$ and $R^5$ are hydrogen.

In one embodiment the present invention provides compounds of formula I, wherein $R^3$ is $Si(CH_3)_3$ or $Si(CH_3)_2CH(CH_3)_2$. In still another embodiment the present invention provides compounds of formula I, wherein $R^3$ is $Si(CH_3)_3$.

In one embodiment the present invention provides compounds wherein $R^6$ is hydrogen.

In one embodiment the present invention provides compounds of formula I, wherein $R^7$ is hydrogen.

In another embodiment the present invention provides compounds of formula I wherein $R^8$ is selected from the group consisting of $C_1$-$C_8$alkyl, $C_2$-$C_8$alkenyl, and halogen-$C_1$-$C_8$alkyl.

In still another embodiment the present invention provides compounds of formula I wherein $R^8$ is heterocyclyl or heteroaryl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen. In still another embodiment the present invention provides compounds of formula I wherein heterocyclyl is tetrahydrothiopyranyl and heteroaryl is selected from furanyl, pyridyl, thiazolyl or thienyl.

In one embodiment the present invention provides compounds of formula I wherein $R^8$ is —$OR^{12}$, and $R^{12}$ is $C_1$-$C_8$alkyl or phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen.

In one embodiment the present invention provides compounds of formula I, wherein $R^8$ is —$NR^{13}R^{14}$, wherein $R^{13}$ and $R^{14}$ independently from each other are selected from hydrogen, $C_1$-$C_8$alkyl, and phenyl which is unsubstituted or substituted by one or two groups independently selected from $C_1$-$C_8$alkyl, $C_1$-$C_8$alkoxy, halogen-$C_1$-$C_8$alkyl, halogen-$C_1$-$C_8$alkoxy and halogen.

In one embodiment the present invention provides compounds of formula I wherein $R^8$ is —C(O)—$OR^{15}$, wherein $R^{15}$ is hydrogen or $C_1$-$C_8$alkyl.

In another embodiment the present invention provides compounds of formula I wherein $R^8$ is phenyl which is unsubstituted or substituted by one or two groups independently selected from $C_1$-$C_8$alkyl, $C_1$-$C_8$ alkoxy, halogen-$C_1$-$C_8$alkyl, halogen-$C_1$-$C_8$alkoxy and halogen. In still another embodiment the present invention provides compounds of formula I-A, wherein $R^8$ is phenyl which is substituted by one or two groups independently selected from halogen-$C_1$-$C_8$alkyl, halogen-$C_1$-$C_8$alkoxy and halogen. In still another embodiment the present invention provides compounds of formula I-A wherein $R^8$ is selected from 3-trifluoromethoxyphenyl, 3-trifluoromethyl, 3-chloro-4-fluoromethyl, 4-fluoro-3-trifluoromethylphenyl, 3-difluoromethoxyphenyl, or 3,4-dichlorophenyl. In still another embodiment the present invention provides compounds of formula I wherein $R^8$ is selected from 3-trifluoromethoxyphenyl, 3-trifluoromethyl, 3-chloro-4-fluoromethyl, 4-fluoro-3-tri-fluoromethylphenyl, 3-difluoromethoxyphenyl, 3-trifluoromethylphenyl and 3,4-dichlorophenyl. In still another embodiment the present invention provides compounds of formula I wherein $R^8$ is 3-trifluoromethylphenyl.

In another embodiment the present invention provides compounds of formula I, wherein at least one of $R^9$, $R^{10}$ and $R^{11}$ is selected from the group consisting of $C_1$-$C_8$alkyl, halogen-$C_1$-$C_8$alkyl or halogen. In still another embodiment the present invention provides compounds of formula I wherein one of $R^9$, $R^{10}$ and $R^{11}$ is selected from halogen-$C_1$-$C_8$alkyl or halogen.

In another embodiment the present invention provides compounds of formula I, wherein $R^{10}$ is halogen. In still another embodiment the present invention provides compounds of formula I wherein halogen means chloro.

In one embodiment the present invention provides compounds of formula I, wherein two of $R^9$, $R^{10}$ and $R^{11}$ are halogen and the other is hydrogen. In another embodiment the present invention provides compounds of formula I, wherein $R^9$ and $R^{10}$ are halogen and $R^{11}$ is hydrogen. In still another embodiment the present invention provides compounds of formula I, wherein $R^9$ is fluorine, $R^{10}$ is chlorine and $R^{11}$ is hydrogen.

The integer n is 1 or 2. In one embodiment the present invention provides compounds of formula I, wherein n is 1.

Furthermore, the pharmaceutically acceptable salts of the compounds of formula I and the pharmaceutically acceptable esters of the compounds of formula I individually constitute also embodiments of the present invention.

Compounds of formula I may form acid addition salts with acids, such as conventional pharmaceutically acceptable acids, e.g., hydrochloride, hydrobromide, phosphate, acetate, fumarate, maleate, salicylate, sulphate, pyruvate, citrate, lactate, mandelate, tartarate, and methanesulphonate, e.g. the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, e.g., racemates, optically pure diastereoisomers, mixtures of diastereoisomers, diastereoisomeric racemates or mixtures of diastereoisomeric racemates. The optically active forms can be obtained, e.g., by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting an acid of the formula II

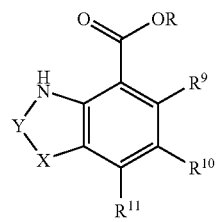
(II)

wherein —X—Y—, $R^9$, $R^{10}$ and $R^{11}$ are as defined herein before and R is hydrogen or $C_1$-$C_8$alkyl, with an amine of formula III

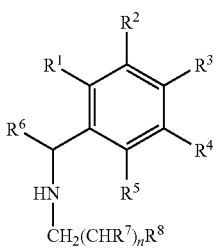
(III)

wherein $R^1$ to $R^8$ and n are as defined herein before, in the presence of a coupling agent; or, alternatively, b) reacting a halogen derivative of formula IV

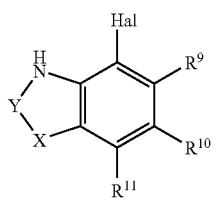
(IV)

wherein —X—Y—, $R^9$, $R^{10}$ and $R^{11}$ are as defined herein before and Hal means halogen, with an amine of formula III in the presence of a suitable catalyst and carbon monoxide, and if desired, converting the compound obtained into a pharmaceutically acceptable acid addition salt.

Examples of coupling reagents include 1-ethyl-3-(3-dimethyl-aminopropyl)-carbodiimide (EDC) or its hydrochloride (EDC.HCl), N,N'-dicyclohexyl-carbodiimide (DCC) or O-(benzotriazol-1-yl)-N,N,N',N'-tetramethyl-uronium-tetrafluoroborate (TBTU).

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

According to reaction scheme 1 formula I compounds may be prepared by coupling of an acid derivative II with an appropriate secondary amine derivative III.

Scheme 1

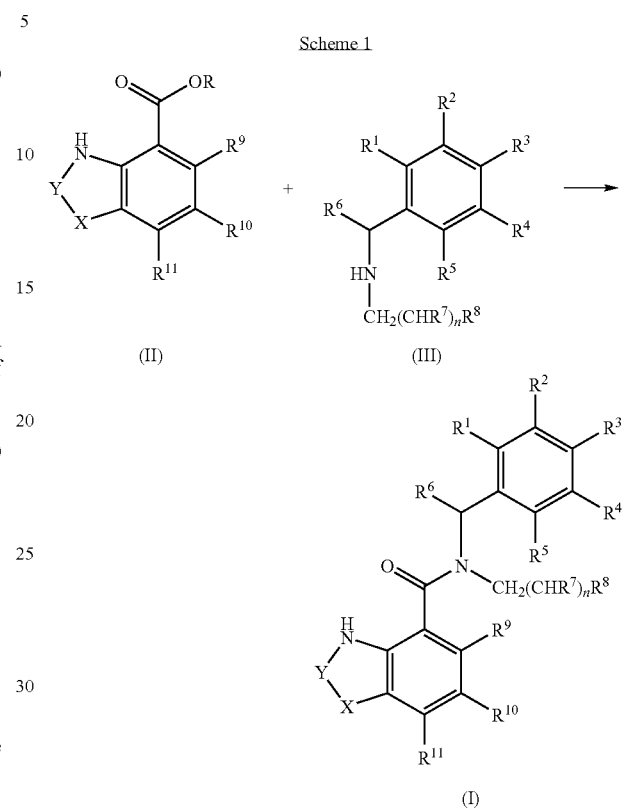

If acids (R═H) of formula II are used in this process, standard peptide coupling reagents can be applied to activate the acid prior to the coupling reaction. Typically, the acid derivative II (R═H) is mixed with a coupling reagent such as EDC or EDC.HCl, DCC or TBTU in an inert solvent such as dimethylformamide (DMF), dimethylacetamide (DMA) or dichloromethane (DCM) together with the appropriate secondary amine derivative III. Optionally a base (e.g. N,N-diisopropylethyl amine, triethylamine, N-methyl morpholine) and/or 1-hydroxybenzotriazole (HOBT) can be added. The reaction mixture is stirred for 1 to 24 h at a temperature of about −30° C. to about 70° C. (e.g. ambient temperature).

Alternatively, esters of formula II (R═$CH_3$ or $C_2H_5$) may be used in the coupling process. In that case, the amine derivative III is treated with trimethylaluminum in an inert solvent such as DCM or toluene at ambient temperature prior to the addition of the ester derivative II.

Acid derivatives of formula II are commercially available or can be prepared following a standard indole, indoline or indazole synthesis as, e.g., described in the general schemes 4 to 7.

Possible routes to synthesize secondary amine derivatives III are outlined in the general schemes 8 to 11 or are given within the example section.

According to scheme 2, compounds of the general formula I may also be prepared by coupling of a halogen derivative IV with an appropriate secondary amine derivative III in the presence of a suitable catalyst (e.g. Pd(dppf)$Cl_2$) and carbon monoxide (e.g. 1 to 100 atmospheres) in an inert solvent (e.g. a mixture of methanol and toluene) at a temperature of about 50° C. to about 150° C.

Possible routes for the synthesis of the necessary halogen derivatives IV are outlined in the general schemes 4, 5 and 9.

of the synthesis. For example, this can be accomplished by sodium borohydride in acetic acid.

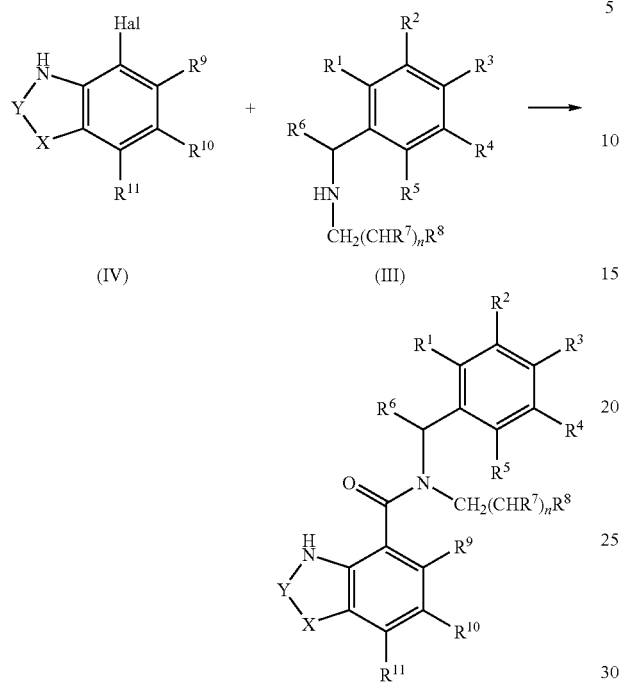

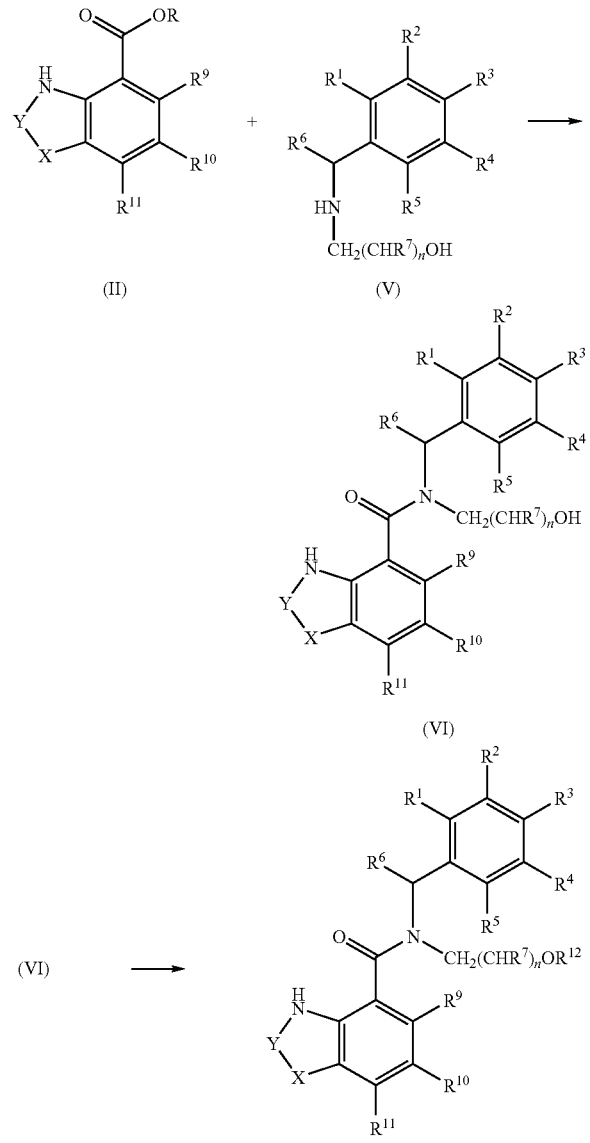

A possible synthesis of compounds of the general formula I wherein $R^8$ represent a group $OR^{12}$ is described in the general scheme 3. In a first step an acid derivative II is coupled with an amine derivative V applying standard peptide coupling conditions (as described for scheme 1). Etherification of the hydroxy group of the intermediate VI to prepare the final compounds can be accomplished using standard methods (e.g. Mitsunobu conditions).

If the appropriate substituents $R^a$ and $R^c$ in compounds of formula I wherein —X—Y— represents —$CR^a$=$CR^c$— are not already present in the acid derivative II or halogen derivative IV that is used in the coupling reaction, they can also be introduced by transformation of a group —CH=$CR^c$—, —$CR^a$=CH— or —CH=CH— into —$CR^a$=$CR^c$— using standard chemistry.

Formula I compounds wherein —X—Y— represents —$CR^aR^b$—$CR^cR^d$— can be prepared either by using the appropriate acid derivative II or halogen derivative IV in the coupling reaction with the amine III or by transformation of a group —$CR^a$=$CR^c$— into —$CR^aR^b$—$CR^cR^d$— at any stage Compounds of formula II and formula IV wherein —X—Y— is —CH=CH— may be prepared as outlined in schemes 4 and 5.

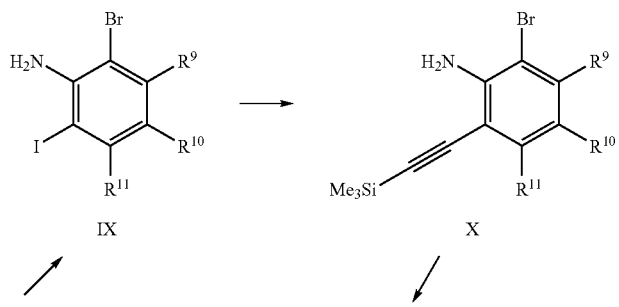

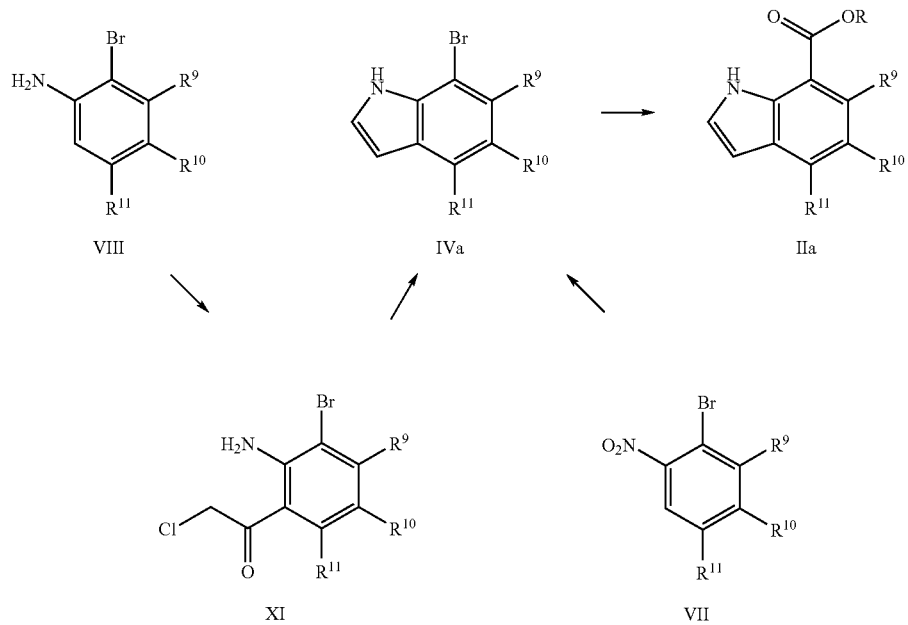

According to scheme 4, compounds of the general formula VII can be converted into indoles of formula IVa in one step. Thus, compounds of formula VII are subjected to an excess of a vinyl Grignard reagent (e.g. 3 equivalents) at low temperature (e.g. at or below −40° C.) in tetrahydrofuran (THF) to prepare bromo-indole compounds of the general structure IVa. Bromo-indoles IVa can be converted into acid derivatives IIa by halogen-metal exchange reaction (e.g. using alkyl-lithium reagents) and trapping of the organometallic intermediate with a suitable electrophile such as carbon dioxide or an alkyl chloroformate. Bromo-indoles IVa can also be reacted with carbon monoxide (e.g. 1 to 100 atmospheres) and an alcohol in the presence of a palladium catalyst (e.g. Pd(dppf)Cl$_2$) to obtain compounds of formula IIa.

Alternatively, compounds of formula IVa and IIa may be prepared starting from anilines with the general structure VIII. Iodination of formula VIII compounds (e.g. with iodine or N-iodosuccinimide) can provide iodo-anilines IX that can be converted into formula X compounds using a Sonogashira coupling reaction. Thus, compounds of formula IX are reacted with ethinyltrimethylsilane in the presence of a palladium catalyst (e.g. Pd(PPh$_3$)$_2$Cl$_2$), copper(I)iodide and an amine base such as triethylamine. The trimethylsilyl protected acetylenes X can either be first deprotected (e.g. with tetrabutyl-ammonium fluoride in THF) and then cyclized to compounds of formula IVa or they can be directly cyclized to compounds of formula IVa using a base such as potassium tert-butoxide in a polar solvent such as N-methylpyrrolidone (NMP).

Compounds of formula IIa and IVa may also be prepared from chloroacetophenone derivatives XI. Thus, aniline derivatives VIII are treated with chloroacetonitrile in the presence of a mixture of boron trichloride and aluminum trichloride in an inert solvent to obtain compounds of formula XI which are then cyclized to indoles IVa by the action of sodium borohydride in dioxane.

Scheme 5

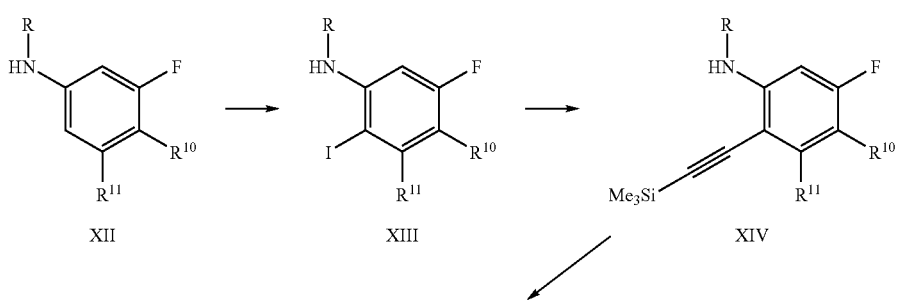

-continued

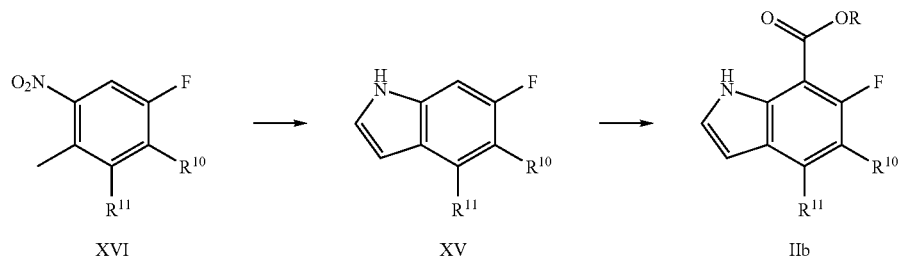

An alternative route for the synthesis of formula II and formula IV compounds wherein —X—Y— is —CH=CH— and R⁹ is fluorine is outlined in scheme 5. Fluoro-anilines XII can be converted into iodo compounds XIII (R=H) using an iodination reagent such as N-iodo-succinimide.

Alternatively a suitable protecting group R such as an alkoxycarbonyl group can be introduced at the aniline nitrogen prior to the iodination step. The protecting group R may be introduced by treatment of a formula XII compound wherein R=H with an appropriate alkyl chloroformate (e.g. methyl or ethyl chloroformate) in an inert solvent in the presence of a base (e.g. sodium bicarbonate). Sonogashira reaction of compounds of formula XIII with ethinyltrimethylsilane results in the formation of acetylenes XIV. Compounds of formula XIV wherein the protecting group R is an alkoxycarbonyl group can be cyclized to indole derivatives XV by treatment with a base (e.g. NaOEt in ethanol) or a fluoride reagent such as tetrabutylammonium fluoride in a solvent such as THF. For compounds of formula XIV wherein R is hydrogen the cyclization to indoles of formula XV can be accomplished using a base such as potassium tert-butoxide in NMP. Alternatively the trimethylsilyl protecting group of the acetylene moiety can be cleaved prior to the cyclization (e.g. with tetrabutylammonium fluoride in THF).

Indoles of formula XV may also be synthesized starting from compounds of formula XVI. Thus, derivatives XVI are treated first with N,N-dimethylformamide dimethylacetal in the presence of a base (e.g. pyrrolidine) and in a second step with hydrogen in the presence of a suitable catalyst (e.g. palladium on charcoal) in a protic solvent such as methanol.

In addition, indoles of formula XV may be prepared from aniline derivatives XII (R=H) by reaction with chloroacetonitrile in the presence of a mixture of boron trichloride and aluminum trichloride and subsequent cyclization using sodium borohydride in dioxane in analogy to the conversion of aniline derivatives VIII into formula IVa compounds as described in scheme 4.

Treatment of indoles of formula XV with an excess of n-butyllithium and potassium tert-butoxide at low temperature (e.g. below −70° C.) results in the formation of an organometallic intermediate that can be reacted with electrophiles such as carbon dioxide or an alkyl chloroformate to form acid derivatives IIb.

Scheme 6

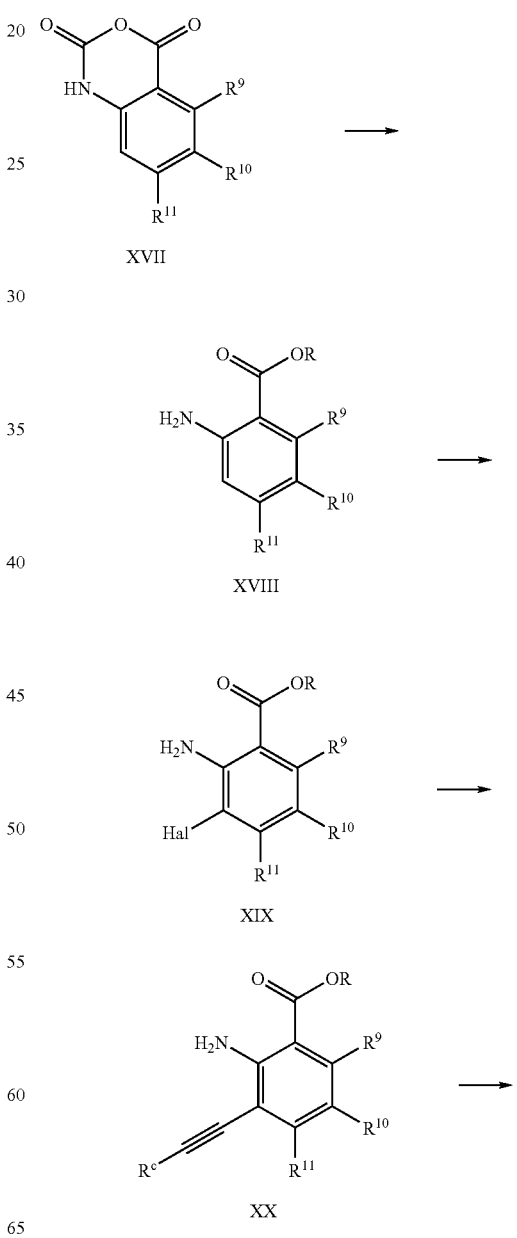

-continued

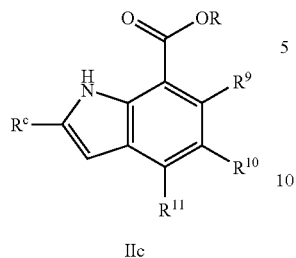

IIc

According to scheme 6 indole derivatives of formula II wherein —X—Y— is —CH=CR$^c$— may be prepared starting from isatoic anhydride derivatives of the general formula XVII. For example compounds of formula XVII can be first converted into anthranilic acid esters XVIII (e.g. with sodium methoxide or with methanol in the presence of DMAP) and then into the halogenated derivatives XIX by treatment with a halogenating agent such as iodine or N-iodosuccinimide. Compounds XIX can then be reacted with the appropriate substituted acetylenes (Sonogashira conditions) to provide compounds of formula XX that are subsequently cyclized to indole derivatives IIc. The cyclisation step can be accomplished either using a base such as potassium tert-butoxide in a solvent such as NMP or by using palladium(II)chloride in a solvent such as acetonitrile. Compounds of formula IIc with R=alkyl can be converted to the corresponding acids (R=H) by treatment with aqueous hydroxide (e.g. lithium or sodium hydroxide) in a polar solvent (e.g. methanol and/or THF).

Scheme 7

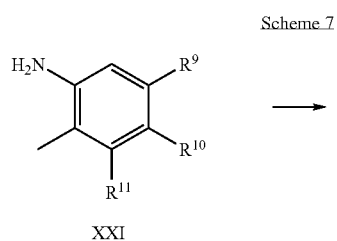

XXI

-continued

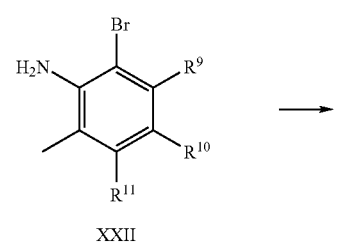

XXII

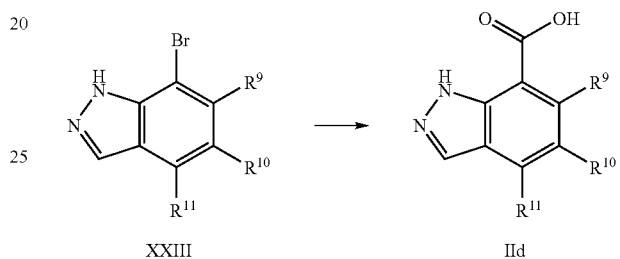

XXIII    IId

Acid derivatives of formula II wherein —X—Y— is —CR$^{12}$=N— may be synthesized as described in scheme 7. Anilines XXI can be brominated to obtain compounds of formula XXII that can be cyclized to indazole derivatives XXIII by treatment with sodium nitrite in acetic acid.

Secondary amines of the general formula III can be synthesized by standard methods. They may be synthesized as outlined in schemes 8 to 11.

Scheme 8

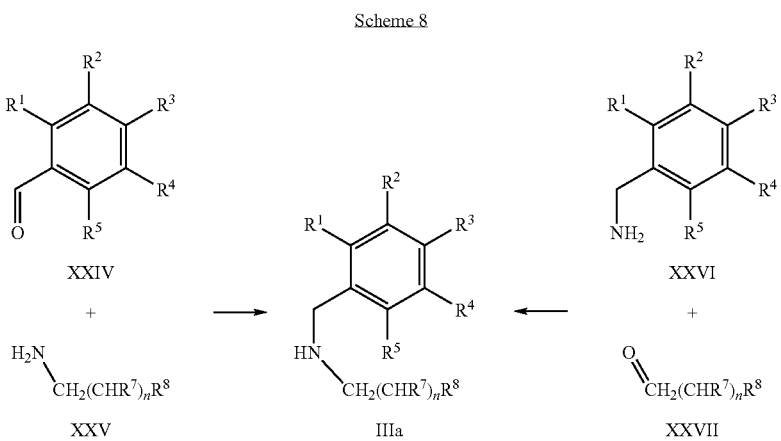

XXIV            IIIa            XXVI

+                              +

XXV                            XXVII

Scheme 8 illustrates a possible synthesis of compounds IIIa ($R^6$=H) either by reductive amination of benzaldehyde derivatives XXIV with amines XXV or by reductive amination of aldehydes XXVII with benzylic amine derivatives XXVI. The necessary starting amines and aldehydes are commercially available or are synthesized using standard methods as e.g. described in the example section.

Secondary amines IIIa may alternatively be synthesized from amide derivatives XXIX or XXXII as outlined in scheme 9.

amines XXV, amides of formula XXXII can be synthesized by coupling benzylic amines XXVI with acids XXXI. These amide couplings can be accomplished using standard coupling reagents and conditions (as described for scheme 1). The necessary starting amines and acids are commercially available or are synthesized using standard conditions as e.g. described in the example section. Alternatively, amide derivatives of formula XXIX can be obtained from compounds of formula XXX wherein X is a halogen atom or a triflate. Thus, compounds of formula XXX are treated with carbon monox

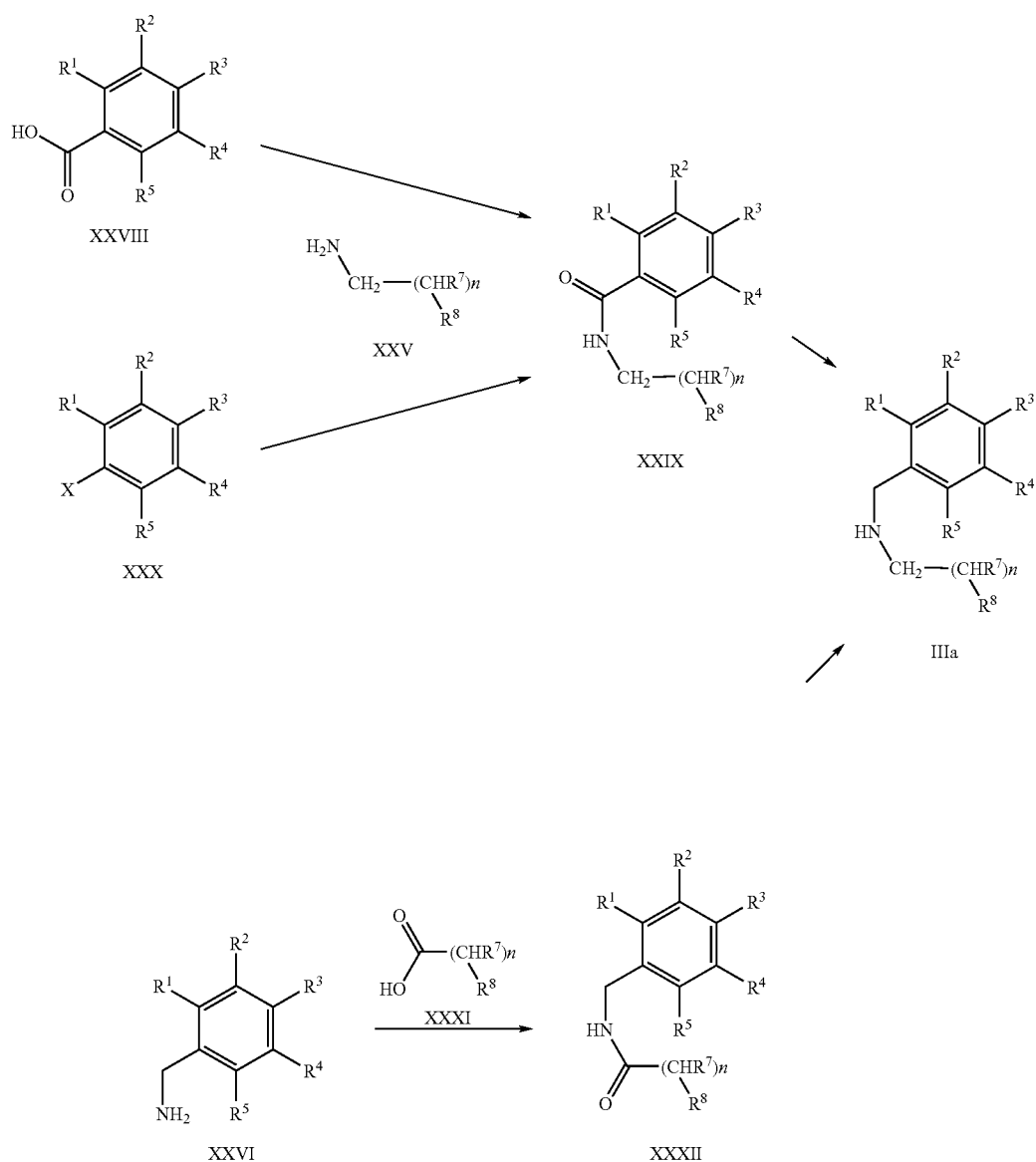

Whereas amide derivatives of formula XXIX are available by the coupling of benzoic acid derivatives XXVIII with ide in the presence of an amine derivative XXV and a suitable catalyst (e.g. Pd(OAc)$_2$ and dppf).

Scheme 10

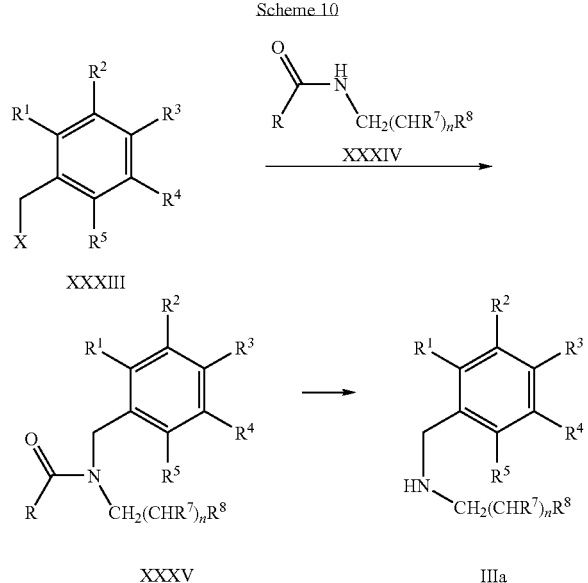

Amines of formula IIIa may also be prepared by alkylation of amide derivatives XXXIV with benzylic halides XXXIII (X=Cl, Br, I) and subsequent cleavage of the amide bond of the intermediates XXXV as described in scheme 10. For example, trifluoroacetamide derivatives XXXIV (R=CF$_3$) can be reacted with a base such as sodium hydride and then with a benzylic halide XXXIII in an inert solvent such as DMF to obtain compounds of formula XXXV (R=CF$_3$). A possible way to cleave the trifluoroacetyl group of the compounds of formula XXXV (R=CF$_3$) is the reaction with sodium borohydride in ethanol.

Scheme 11

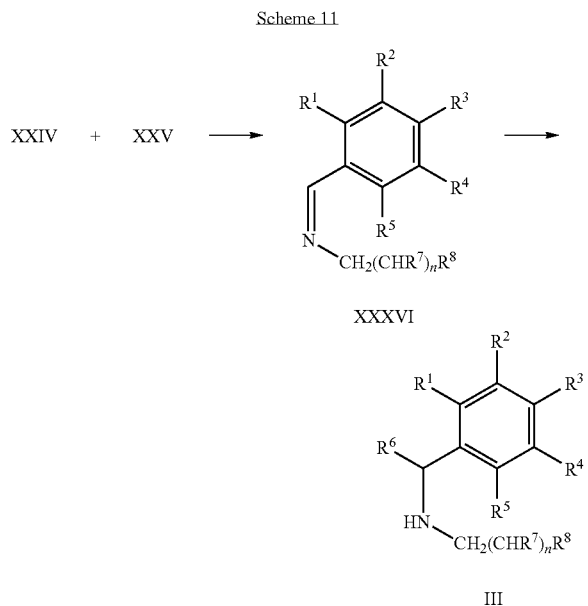

Secondary amines III may also be synthesized from imines XXXVI by the reaction with an alkyllithium reagent R$^6$Li (e.g. methyllithium) in the presence of a Lewis acid such as boron trifluoride ethyl etherate. Imines XXXVI are accessible from aldehydes XXIV and amines XXV by standard methods.

The following examples illustrate the invention.

In general, the nomenclature used in this Application is based on AUTONOM™ v.4.0, a Beilstein Institute computerized system for the generation of IUPAC systematic nomenclature.

EXAMPLE 1

Preparation of 5-Chloro-6-fluoro-1H-indole-7-carboxylic acid [2-(3-trifluoromethoxy-phenyl)-ethyl]-(4-trimethylsilanyl-benzyl)-amide To a solution of 5-chloro-6-fluoro-1H-indole-7-carboxylic acid (64 mg, 0.3 mmol), (4-tert-butyl-benzyl)-[2-(3-trifluoromethoxy-phenyl)-ethyl]-amine (92 mg, 0.25 mmol) and N-methyl morpholine (76 mg, 0.75 mmol) in DMF (3 ml) was added HBTU (142 mg, 0.375 mmol). After stirring the reaction mixture over night at rt it was diluted with water and extracted twice with diethyl ether. The combined organic phases were washed twice with 1N aq. NaOH solution, twice with 1N aq. HCl solution and once with sat. aq. NaCl solution, dried over sodium sulfate, filtered and concentrated in vacuo. The remaining oil was purified by preparative HPLC to give 5-chloro-6-fluoro-1H-indole-7-carboxylic acid [2-(3-trifluoromethoxy-phenyl)-ethyl]-(4-trimethylsilanyl-benzyl)-amide (36 mg, 26%) as a white solid. MS (ISP) 563.4 (M+H)$^+$.

Preparation of
5-chloro-6-fluoro-1H-indole-7-carboxylic Acid

4-Chloro-3-fluoro-phenylamine (10 g, 68.7 mmol) was dissolved in dichloromethane (38 ml) and treated with sodium bicarbonate (6.82 g, 72.1 mmol) in water (100 ml). At rt methyl chloroformate (8 ml, 103.0 mmol) was added dropwise over a period of 25 min (temperature raises from 22 to 28° C.). After 1.5 h stirring at rt, the reaction mixture was diluted with dichloromethane (100 ml). After separation, the organic phase was washed with sat. aq. NaCl solution (45 ml), dried over magnesium sulfate, filtered and diluted with hexane (140 ml). The dichloromethane was then removed under vacuo and the resulting suspension filtered leading to (4-chloro-3-fluoro-phenyl)-carbamic acid methyl ester (13 g, 92%) as a white powder. MS (EI) 203.1 (M)$^+$.

(4-Chloro-3-fluoro-phenyl)-carbamic acid methyl ester (5.34 g, 26.2 mmol) was dissolved in acetonitrile (50 ml) and treated with N-iodosuccinimide (6.49 g, 28.9 mmol) and tri-fluoromethanesulfonic acid (0.23 ml, 2.6 mmol) under nitrogen and stirred at rt for 3 hours. The reaction mixture was then poured on sat. aq. sodium bicarbonate solution (50 ml), extracted twice with ethyl acetate. The combined organic phases were then washed with sat. aq. NaCl solution, dried over magnesium sulfate, filtered and concentrated in vacuo, leading to (4-chloro-5-fluoro-2-iodo-phenyl)-carbamic acid methyl ester (8.2 g, 95%) as a dark blue powder. MS (EI) 328.9 (M)$^+$.

Pd(PPh$_3$)$_2$Cl$_2$ (153 mg, 0.22 mmol) and copper(I)iodide (42 mg, 0.22 mmol) were dissolved in triethylamine (40 ml) and refluxed under argon for 20 min. The reaction mixture was then cooled down to 0° C. and (4-chloro-5-fluoro-2-iodo-phenyl)-carbamic acid methyl ester (7.2 g, 21 mmol) was added. After 10 min stirring at rt, ethinyltrimethylsilane (3.45 ml, 24.9 mmol) was added dropwise (exothermic, temperature raises from 18 to 33° C.) and the reaction mixture was stirred for one hour at rt. The reaction mixture was then poured on 1N aq. HCl solution (180 ml) and ice and extracted twice with ethyl acetate (180 ml). The combined organic phases were washed with water and sat. aq. NaCl solution, dried over magnesium sulfate, filtered and concentrated in vacuo to yield crude (4-chloro-5-fluoro-2-trimethylsilanyl-ethynyl-phenyl)-carbamic acid methyl ester.

The crude (4-chloro-5-fluoro-2-trimethylsilanylethynyl-phenyl)-carbamic-acid methyl ester (ca 21 mmol) was dissolved in THF (200 ml) and treated with tetrabutylammonium fluoride (43.3 ml, 1M in THF, 43.3 mmol) at rt. After 5 min stirring at rt, the reaction mixture was refluxed for one hour under argon. The reaction mixture was then cooled down to rt and concentrated in vacuo. The resulting oil was treated with water (55 ml), stirred for 10 min and finally extracted twice with ethyl acetate (100 ml). The combined organic phases were sequentially washed with 1M aq. HCl solution (50 ml) sat. aq. sodium bicarbonate solution (50 ml), sat. aq. NaCl solution (50 ml) and finally dried over magnesium sulfate, filtered and concentrated in vacuo. The residue was stirred with hexane (200 ml) under reflux, cooled to 5° C. and filtered leading to 5-chloro-6-fluoro-1H-indole (3.15 g, 85%) as a light brown solid. MS (EI) 169.1 (M)$^+$.

THF (35 ml) was cooled down to −75° C. under argon and a 1.6M solution of n-butyllithium in hexane (19.05 ml, 30.5 mmol) was added. Then a solution of 5-chloro-6-fluoro-1H-indole (2.35 g, 13.7 mmol) in THF (9 ml) was added over 15 min dropwise keeping the temperature between −70 and −75° C. After additional 5 min stirring at this temperature a solution of potassium tert-butylate (3.7 g) in THF (15 ml) was added over 10 min keeping the temperature between −70 and −75° C. The brown solution was stirred 2 hours at the same temperature and then treated with a large excess of solid carbon dioxide. The temperature was then raised to 10° C. over a period of 75 min, and the reaction was treated with water (30 ml). After separation of the organic phase, the aqueous phase was extracted twice with diethylether (20 ml), treated with concentrated aq. HCl solution until pH 1. The suspension was then filtered, the solid washed with water and dried in high vacuo. The residue was stirred with hexane/diethylether (9/1, 10 ml) for 15 min and filtered, washed with the same solvent mixture (5 ml) and the collected solid dried in high vacuo, leading to 5-chloro-6-fluoro-1H-indole-7-carboxylic acid (2.2 g, 75%) as a light brown solid. MS (ISP): 212.2 (M−H)$^−$.

Preparation of 4-trimethylsilanyl-benzaldehyde

1-Bromo-4-(trimethylsilyl)benzene (1.15 g, 5 mmol) was dissolved in THF (30 ml) and cooled to −78° C. Under argon a 1.6 M solution of n-butyl lithium in hexane (3.13 ml, 5 mmol) was added dropwise keeping the temperature below −70° C. The clear colorless solution was stirred at −78° C. for 15 min and DMF (1.16 ml, 15 mmol) was added quickly. The reaction temperature raised to −68° C. The reaction was stirred for additional 15 min at −78° C., quenched with 1N aq. HCl solution and extracted twice with diethyl ether. The combined organic layers were washed twice with water and once with sat. aq. NaCl solution, dried over sodium sulfate, filtered and the solvent was evaporated to yield 4-trimethyl-silanyl-benzaldehyde (920 mg, 100%) as a colorless oil. The product was pure enough to be used directly in the next step. MS (ISP): 179.2 (M+H)$^+$. $^1H$NMR (CDCl$_3$, 300 MHz): δ 10.02 (s, 1H) 7.84 (d, 2H), 7.69 (d, 2H), 0.31 (s, 9H).

Preparation of [2-(3-trifluoromethoxy-phenyl)-ethyl]-(4-trimethylsilanyl-benzyl)-amine:

(3-Trifluoromethoxy-phenyl)-acetonitrile (10.4 g, 52 mmol) was dissolved in THF (83 ml) and cooled down to 0° C. under nitrogen. 1M borane-THF complex solution in THF (274 ml, 274 mmol) was then added dropwise over 55 min keeping the temperature between 0-2° C. After addition the reaction mixture was stirred at rt for additional 45 min, and then refluxed for 17 h. The reaction mixture was then cooled down to 0° C. and treated between 2 and 5° C. with methanol (62 ml) over a period of 30 min. After 1 h refluxing the reaction mixture was concentrated in vacuo, the remaining residue dissolved in methylene chloride and the mixture was extracted twice with 1N aq. HCl solution. The combined aqueous phases were then treated with concentrated aq. NaOH solution to adjust the pH to 12, and then extracted twice with methylene chloride. The combined organic phases were then washed with water, dried over magnesium sulfate, filtered and concentrated in vacuo leading to a colorless oil (8.6 g). This was dissolved in diethylether (200 ml), treated with 2.6N HCl solution in diethylether (20 ml), stirred at rt for additional 1 h, filtered, washed with diethylether and dried under vacuo, leading to 2-(3-trifluoromethoxy-phenyl)-ethylamine hydrochloride (2.34 g, 65%) as a white solid. MS (ISP) 206.1 (M+H)$^+$.

4-Trimethylsilanyl-benzaldehyde (178 mg, 1 mmol), 2-(3-trifluoromethoxy-phenyl)-ethyl-amine hydrochloride (241 mg, 1.1 mmol) and triethyl amine (151 mg, 1.5 mmol) were dissolved in methanol (5 ml) and the solution was stirred at rt for 5 min. Sodium borohydride (37 mg, 1 mmol) was added under nitrogen and the reaction mixture was stirred at rt for 1 h. Water was added and methanol was evaporated in vacuo. The reaction was extracted twice with diethyl ether and the combined organic layers were washed once with water and once with sat. aq. NaCl solution, dried with sodium sulfate, filtered off and concentrated in vacuo to yield [2-(3-trifluoromethoxy-phenyl)-ethyl]-(4-trimethylsilanyl-benzyl)-amine (370 mg, 100%) as a colorless oil. MS (ISP) 368.2 (100) (M+H)$^+$.

EXAMPLE 2

Preparation of 5-Chloro-6-fluoro-1H-indole-7-carboxylic acid [2-(3,4-dichloro-phenyl)-ethyl]-(4-trimethylsilanyl-benzyl)-amide 5-Chloro-6-fluoro-1H-indole-7-carboxylic acid [2-(3,4-dichloro-phenyl)-ethyl]-(4-trimethylsilanyl-benzyl)-amide was prepared in analogy to example 1 from 5-chloro-6-fluoro-1H-indole-7-carboxylic acid and [2-(3,4-dichloro-phenyl)-ethyl]-(4-trimethylsilanyl-benzyl)-amine. MS (ISP) 547.2/549.3/551.3 (96/100/37) (M+H)$^+$.

Preparation of [2-(3,4-dichloro-phenyl)-ethyl]-(4-trimethylsilanyl-benzyl)-amine:

4-Trimethylsilanyl-benzaldehyde (800 mg, 4.5 mmol) and 2-(3,4-dichloro-phenyl)-ethylamine (1023 mg, 5.4 mmol) were dissolved in methanol (5 ml) and the solution was stirred at rt for 5 min. Sodium borohydride (166 mg, 4.5 mmol) was added under nitrogen and the reaction mixture was stirred at rt for 1 h. Water was added and methanol was evaporated in vacuo. The reaction was extracted twice with diethyl ether and the combined organic layers were washed once with water and once with sat. aq. NaCl solution, dried with sodium sulfate, filtered and concentrated in vacuo to yield [2-(3,4- dichloro-phenyl)-ethyl]-(4-trimethylsilanyl-benzyl)-amine (1640 mg, 100%) as a colorless oil. MS (ISP): 352.2/354.2 (100/74) (M+H)+. $^{1H}$NMR (CDCl$_3$, 300 MHz): δ 7.48 (d, 2H), 7.25-7.35 (m, 4H), 7.02 (dd, 2H), 3.79 (s, 2H), 2.75-3.00 (m, 4H), 0.26 (s, 9H).

EXAMPLE 3

Preparation of 5-Chloro-6-fluoro-1H-indole-7-carboxylic acid [2-(3-trifluoromethyl-phenyl)-ethyl]-(4-trimethylsilanyl-benzyl)-amide 5-Chloro-6-fluoro-1H-indole-7-carboxylic acid [2-(3-trifluoromethyl-phenyl)-ethyl]-(4-trimethylsilanyl-benzyl)-amide was prepared in analogy to example 1 from 5-chloro-6-fluoro-1H-indole-7-carboxylic acid and [2-(3-trifluoromethyl-phenyl)-ethyl]-(4-trimethylsilanyl-benzyl)-amine. MS (ISP) 547.3/549.4 (100/33) (M+H)+.

Preparation of [2-(3-trifluoromethyl-phenyl)-ethyl]-(4-trimethylsilanyl-benzyl)-amine:

[2-(3-trifluoromethyl-phenyl)-ethyl]-(4-trimethylsilanyl-benzyl)-amine was prepared in analogy to example 1 from 4-trimethylsilanyl-benzaldehyde and 2-(3-trifluoromethyl-phenyl)-ethylamine. MS (ISP): 352.3 (M+H)+. $^{1H}$NMR (CDCl$_3$, 300 MHz): δ 7.48 (m, 4H), 7.39 (m, 2H), 7.27 (d, 2H), 3.81 (s, 2H), 2.80-3.00 (m, 4H), 0.26 (s, 9H).

EXAMPLE 4

Preparation of 5-Chloro-6-fluoro-1H-indole-7-carboxylic Acid [2-(4-chloro-phenyl)-ethyl]-(4-trimethylsilanyl-benzyl)-amide 5-Chloro-6-fluoro-1H-indole-7-carboxylic acid [2-(4-chloro-phenyl)-ethyl]-(4-trimethylsilanyl-benzyl)-amide was prepared in analogy to example 1 from 5-chloro-6-fluoro-1H-indole-7-carboxylic acid and [2-(4-chloro-phenyl)-ethyl]-(4-trimethylsilanyl-benzyl)-amine. MS (ISP) 513.3/515.3 (100/69) (M+H)+.

Preparation of [2-(4-chloro-phenyl)-ethyl]-(4-trimethylsilanyl-benzyl)-amine:

[2-(4-chloro-phenyl)-ethyl]-(4-trimethylsilanyl-benzyl)-amine was prepared in analogy to example 1 from 4-trimethylsilanyl-benzaldehyde and 2-(4-chloro-phenyl)-ethylamine. MS (ISP): 318.1/320.3 (100/39) (M+H)+. $^{1H}$NMR (CDCl$_3$, 300 MHz): δ 7.47 (d, 2H), 7.23-7.28 (m, 4H), 7.12 (d, 2H), 3.79 (s, 2H), 2.75-3.00 (m, 4H), 0.26 (s, 9H).

EXAMPLE 5

Preparation of 5-Chloro-6-fluoro-1H-indole-7-carboxylic Acid [2-(4-fluoro-phenyl)-ethyl]-(4-trimethylsilanyl-benzyl)-amide 5-Chloro-6-fluoro-1H-indole-7-carboxylic acid [2-(4-fluoro-phenyl)-ethyl]-(4-trimethylsilanyl-benzyl)-amide was prepared in analogy to example 1 from 5-chloro-6-fluoro-1H-indole-7-carboxylic acid and [2-(4-fluoro-phenyl)-ethyl]-(4-trimethylsilanyl-benzyl)-amine. MS (ISP) 497.4/499.3 (100/48) (M+H)+.

Preparation of [2-(4-fluoro-phenyl)-ethyl]-(4-trimethylsilanyl-benzyl)-amine:

[2-(4-fluoro-phenyl)-ethyl]-(4-trimethylsilanyl-benzyl)-amine was prepared in analogy to example 1 from 4-trimethylsilanyl-benzaldehyde and 2-(4-fluoro-phenyl)-ethylamine. MS (ISP): 302.2 (100) (M+H)+. $^{1H}$NMR (CDCl$_3$, 300 MHz): δ 7.47 (d, 2H), 7.27 (d, 2H), 7.15 (dd, 2H), 6.97 (dt, 2H) 3.79 (s, 2H), 2.75-3.00 (m, 4H), 0.26 (s, 9H).

EXAMPLE 6

Preparation of 5-Chloro-6-fluoro-1H-indole-7-carboxylic Acid [4-(isopropyl-dimethyl-silanyl)-benzyl]-[2-(3-trifluoromethyl-phenyl)-ethyl]-amide 5-Chloro-6-fluoro-1H-indole-7-carboxylic acid [4-(isopropyl-dimethyl-silanyl)-benzyl]-[2-(3-trifluoromethyl-phenyl)-ethyl]-amide was prepared in analogy to example 1 from 5-chloro-6-fluoro-1H-indole-7-carboxylic acid and [4-(isopropyl-dimethyl-silanyl)-benzyl]-[2-(3-trifluoromethyl-phenyl)-ethyl]-amine. MS (ISP) 575.3/576.4/577.3 (100/46/40) (M+H)+.

Preparation of 4-(isopropyl-dimethyl-silanyl)-benzaldehyde:

1,4-Dibromo-benzene (1.18 g, 5 mmol) was dissolved in THF (15 ml) and cooled to −78° C. Under argon a 1.6 M solution of n-butyl lithium in hexane (3.13 ml, 5 mmol) was added slowly under stirring keeping the temperature below −70° C. After complete addition the reaction was stirred at −78° C. for 30 min and dimethyl-isopropyl-silylchloride (683 mg, 5 mmol) was added carefully keeping the temperature again below −70° C. The reaction was stirred at −78° C. for 30 min and a 1.6 M solution of n-butyl lithium in hexane (3.13 ml, 5 mmol) was added at this temperature keeping the temperature below −70° C. After stirring for 30 min at −78° C. DMF (1.1 g, 15 mmol) was added in one portion and the reaction was allowed to warm to rt. Water was added and the solvent was evaporated. The reaction was extracted twice with diethylether. The combined organic layers were dried over sodium sulfate, filtered and the solvent was evaporated, to yield 4-(isopropyl-dimethyl-silanyl)-benzaldehyde (900 mg, 87%) as a colorless oil. The product was pure enough to be used directly in the next step. MS (ISP): 207.1 (M+H)+. $^{1H}$NMR (CDCl$_3$, 300 MHz): δ 10.0 (s, 1H), 7.84 (d, J=8.1 Hz, 2H), 7.67 (d, J=8.1 Hz, 2H), 0.93-0.99 (m, 7H), 0.28 (s, 6H).

Preparation of [4-(Isopropyl-dimethyl-silanyl)-benzyl]-[2-(3-trifluoromethyl-phenyl)-ethyl]-amine:

[4-(Isopropyl-dimethyl-silanyl)-benzyl]-[2-(3-trifluoromethyl-phenyl)-ethyl]-amine was prepared in analogy to example 1 from 4-(isopropyl-dimethyl-silanyl)-benzaldehyde and 2-(3-trifluoromethyl-phenyl)-ethylamine. MS (ISP): 380.2 (100) (M+H)+. $^{1H}$NMR (CDCl$_3$, 300 MHz): δ 7.52-7.42 (m, 6H), 7.26 (d, J=7.8 Hz, 2H), 3.81 (s, 2H), 2.88-2.96 (m, 4H), 0.95 (m, 7H), 0.23 (s, 6H).

The compounds of formula I are cholesteryl ester transfer protein (CETP) inhibitors.

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are three different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

Plasma lipoprotein metabolism can be described as a flux of cholesterol between liver and the other tissues. The LDL pathway corresponds to the secretion of VLDL from the liver to deliver cholesterol by LDL to tissues. Any alteration in LDL catabolism could lead to uptake of excess cholesterol in the vessel wall forming foam cells and atherosclerosis. The opposite pathway is the mobilization of free cholesterol from peripheral tissues by HDL to deliver cholesterol to the liver to be eventually excreted with bile. In humans a significant part of cholesteryl ester (CE) is transferred from HDL to the VLDL, LDL pathway. This transfer is mediated by a 70,000 dalton plasma glycoprotein, the cholesteryl ester transfer protein (CETP).

Mutations in the CETP gene associated with CETP deficiency are characterized by high HDL-cholesterol levels (>60 mg/dL) and reduced cardiovascular risk. Such findings are consistent with studies of pharmacologically mediated inhibition of CETP in the rabbit, which argue strongly in favor of CETP inhibition as a valid therapeutic approach [Le Goff et al., Pharmacology & Therapeutics 101:17-38 (2004); Okamoto et al., Nature 406:203-207 2000)].

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well tolerated agent which can significantly elevate plasma HDL levels. The net result of CETP activity is a lowering of HDL-C and an increase in LDL-C. This effect on lipoprotein profile is believed to be pro-atherogenic, especially in subjects whose lipid profile constitutes an increased risk for coronary heart disease. Therefore by inhibiting CETP activity there is the potential to inverse this relationship towards a lower risk and ultimately to protect against coronary heart diseases and associated mortality.

Thus, CETP inhibitors are useful as medicaments for the treatment and/or prophylaxis of atherosclerosis, peripheral vascular disease, dyslipidemia, hyperbeta-lipoproteinemia, hypoalphalipoproteinemia, hypercholesterolemia, hypertriglyceridemia, familial hyper-cholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, CETP inhibitors may be used in combination with another compound, said compound being an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

As described above, the compounds of formula I of the present invention can be used as medicaments for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use as medicament for the treatment and/or prevention of dyslipidemia is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hyper-cholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia is preferred.

The invention further relates to the use of compounds of formula I as defined above for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the treatment and/or prophylaxis of dyslipidemia is preferred.

In addition, the invention relates to the use of compounds of formula I as defined above for the preparation of medicaments for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the preparation of medicaments for the treatment and/or prophylaxis of dyslipidemia is preferred.

In addition, CETP inhibitors are useful in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

The invention therefore also relates to pharmaceutical compositions comprising a compound of formula I as defined above in combination with an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant, as well as a pharmaceutically acceptable carrier and/or adjuvant.

The invention further relates to the use of compounds of formula I as defined above in combination with an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant for the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia, as well as to the use of such a combination for the preparation of corresponding medicaments.

The compounds of formula I and their pharmaceutically acceptable salts possess valuable pharmacological properties. Specifically, it has been found that the compounds of the present invention are inhibitors of the cholesteryl ester transfer protein (CETP).

The following tests were carried out in order to determine the activity of the compounds of formula I.

Activity of CETP inhibitors was determined using a buffer assay system. Partially purified CETP transferred radiolabeled cholesteryl ester from HDL donor particles to biotin-labeled LDL acceptor particles. The reaction was stopped by addition of streptavidin-coupled scintillation proximity assay (SPA) beads. These beads captured the biotinylated acceptor particles and transferred radioactivity was measured. The assay system was purchased and performed according to manufacturer's recommendations (Amersham Biosciences). Inhibitory activity of compounds was determined as percentage of positive control activity containing CETP together with donor and acceptor particles. Serial dilution of compounds was performed in order to determine the $IC_{50}$ values.

Activity of the compounds was subsequently measured in the presence of plasma using the same assay as described above except that the source of CETP was human lipoprotein-deprived serum (LPDS). Inhibitory activity of compounds was determined as percentage of positive control activity containing all the assay components except compound. Serial dilution of compounds was performed in order to determine the $IC_{50}$ values.

Under the latter assay conditions, the compounds of the present invention exhibit $IC_{50}$ values within the range of about 1 nM to about 10 µM, e.g., of about 1 nM to about 1 µM, e.g., of about 1 nM to about 200 nM. The following table shows measured values for some selected compounds of the present invention.

|  | $IC_{50}$ (nM) |
| --- | --- |
| Example 1 | 21 |
| Example 3 | 16 |
| Example 6 | 44 |

In vivo activity of the compounds of formula I were determined in hamster using the following protocol:

Male golden Syrian hamsters (6-week-old, 100-130 g) under standard chow diet received compounds in the morning by oral gavage using appropriate vehicle, blood was taken 2 h later by retro-orbital bleeding under isofluran anaesthesia and 7 h later on sacrificed animals. Plasma was separated from blood using low speed centrifugation and CETP activity was measured in plasma using the radioactive CETP activity assay as described above except that diluted plasma replaced LPDS. In vivo CETP inhibition was expressed as CETP activity remaining in the plasma of treated animals as compared to plasma CETP activity of placebo treated animals.

Efficacy of compounds in modulating plasma lipid levels can be determined in hamsters after 7 days of daily administration of compounds. Male hamsters are acclimated for 3-4 days to receive food as a paste made of 10 g chow and 10 g water per day. Compounds are then mixed within this paste and a portion containing the proper amount of compounds is given every morning for 7 days. Alternatively compounds can be given by oral gavage using the proper vehicle. Blood is taken before compound treatment by retro-orbital bleeding and at the end of the treatment on sacrificed animals. Plasma is separated from blood by low speed centrifugation and selected organs are taken (e.g. liver, fat, brain, etc.). Effects of compounds on plasma lipid levels are determined by measuring total cholesterol, HDL-cholesterol, LDL-cholesterol and triglyceride using colorimetric enzymatic assays (Roche Diagnostic GmbH, Mannheim, Germany). HDL-C, LDL-C and VLDL-C are e.g., quantified using size exclusion chromatography on superpose-6 column using SMART™ system (Pharmacia). Lipoprotein distribution is calculated assuming a Gaussian distribution for each peak, using a non-linear, least-squares curve-fitting procedure to calculate the area under the curve. Plasma samples are also used to quantify CETP activity as described above. Compound concentration is also determined in plasma and selected tissues as liver, fat, heart, muscle and brain.

Efficacy of compounds in modulating plasma lipid levels can be also determined in cholesterol/fat fed hamsters. The protocol is identical as described above except that animals are fed with chow diet enriched with 10% (w/w) saturated fat and 0.05% (w/w) cholesterol. Animals receive this high fat diet 2 weeks before starting compound administration and continue this diet throughout the study. The 2 weeks pre-treatment induces an increase in plasma cholesterol and triglyceride levels allowing a better assessment of LDL-C and triglyceride lowering.

Efficacy of compounds in its ability to acutely raise HDL-C is assessed in cynomolgus monkeys. Animals are fed with standard primate maintenance diet. Compounds are formulated with appropriate vehicle and administered to animals by oral gavage. Blood is taken before and at several time-points after compound administration (usually 30 min, 1 h, 2 h, 4 h, 7 h and 24 h). Plasma is separated from blood by low speed centrifugation and CETP activity and plasma lipids are quantified. Compound potency and efficacy can be assessed by measuring the HDL-C increase after this single-dose administration. In such pharmacodynamic model the extent together with the kinetics of the pharmacologic effect can be assessed.

The compounds of formula I and their pharmaceutically acceptable salts and esters can be used as medicaments, e.g. in the form of pharmaceutical preparations for enteral, parenteral or topical administration. They can be administered, e.g., perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, e.g., lactose, corn starch or derivatives thereof, talc, stearic acid or its salts can be used as carrier materials for tablets, coated tablets, dragées and hard gelatine capsules. Suitable carrier materials for soft gelatine capsules are, e.g., vegetable oils, waxes, fats and semi-solid and liquid polyols (depending on the nature of the active ingredient no carriers are, however, required in the case of soft gelatine capsules). Suitable carrier materials for the production of solutions and syrups are, e.g., water, polyols, sucrose, invert sugar and the like. Suitable carrier materials for injection solutions are, e.g., water, alcohols, polyols, glycerol and vegetable oils. Suitable carrier materials for suppositories are, e.g., natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, e.g., 0.5-100 mg, of a compound of formula I.

The following examples serve to illustrate the present invention in more detail. They are, however, not intended to limit its scope in any manner.

EXAMPLE A

Film Coated Tablets

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

EXAMPLE B

Capsules

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

EXAMPLE C

Injection Solutions

| | |
|---|---|
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

EXAMPLE D

Soft Gelatin Capsules

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |

| Gelatin capsule | |
|---|---|
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

The invention claimed is:

1. A compound of formula I

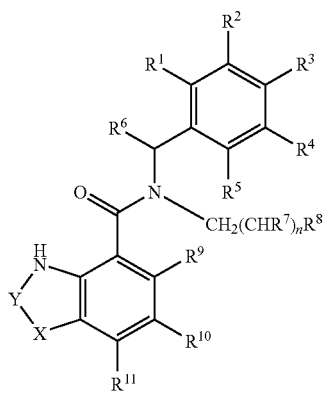

wherein
—X—Y— is —CR$^a$=CR$^c$— or —CR$^a$=N— or —CR$^a$R$^b$—CR$^c$R$^d$—,
wherein R$^a$, R$^b$, R$^c$ and R$^d$ are independently from each other selected from the group consisting of hydrogen and C$_1$-C$_8$alkyl;
R$^1$, R$^2$, R$^4$ and R$^5$ are independently from each other selected from the group consisting of hydrogen, C$_1$-C$_8$alkyl, C$_1$-C$_8$alkoxy, halogen and halogen-C$_1$-C$_8$alkyl;
R$^3$ is Si(C$_1$-C$_6$alkyl)$_3$;
R$^6$ is selected from the group consisting of hydrogen and C$_1$-C$_8$alkyl;
R$^7$ is selected from the group consisting of hydrogen, C$_1$-C$_8$alkyl, hydroxy and halogen;
R$^8$ is selected from the group consisting of C$_1$-C$_8$alkyl, C$_2$-C$_8$alkenyl, halogen-C$_1$-C$_8$alkyl, heterocyclyl, heteroaryl which is unsubstituted or substituted by one or two groups independently selected from C$_1$-C$_8$alkyl, C$_1$-C$_8$alkoxy, halogen-C$_1$-C$_8$alkyl, halogen-C$_1$-C$_8$alkoxy and halogen, phenyl which is unsubstituted or substituted by one or two groups independently selected from C$_1$-C$_8$alkyl, C$_1$-C$_8$alkoxy, halogen-C$_1$-C$_8$alkyl, halogen-C$_1$-C$_8$alkoxy and halogen, —OR$^{12}$, wherein R$^{12}$ is C$_1$-C$_8$alkyl or phenyl which is unsubstituted or substituted by one or two groups independently selected from C$_1$-C$_8$alkyl, C$_1$-C$_8$alkoxy, halogen-C$_1$-C$_8$alkyl, halogen-C$_1$-C$_8$alkoxy and halogen, —NR$^{13}$R$^{14}$, wherein R$^{13}$ and R$^{14}$ independently from each other are selected from hydrogen, C$_1$-C$_8$alkyl, and phenyl which is unsubstituted or substituted by one or two groups independently selected from C$_1$-C$_8$alkyl, C$_1$-C$_8$alkoxy, halogen-C$_1$-C$_8$alkyl, halogen-C$_1$-C$_8$alkoxy and halogen, and —C(O)—OR$^{15}$, wherein R$^{15}$ is hydrogen or C$_1$-C$_8$alkyl;

R$^9$, R$^{10}$ and R$^{11}$ independently from each other are selected from the group consisting of hydrogen, C$_1$-C$_8$alkyl, cycloalkyl, C$_1$-C$_8$alkoxy, halogen-C$_1$-C$_8$alkyl, and halogen;
n is 1, 2 or 3;
and all pharmaceutically acceptable salts thereof.

2. The compound of claim 1 wherein R$^3$ is Si(CH$_3$)$_3$ or Si(CH$_3$)$_2$CH(CH$_3$)$_2$.

3. The compound of claim 1 wherein X—Y is —CR$^a$=CR$^c$—.

4. The compound of claim 1 wherein X—Y is —CR$^a$=N—.

5. The compound of claim 1 wherein X—Y is —CR$^a$R$^b$—CR$^c$R$^d$—.

6. The compound of claim 3 wherein R$^3$ is Si(CH$_3$)$_3$ or Si(CH$_3$)$_2$CH(CH$_3$)$_2$.

7. The compound of claim 4 wherein R$^3$ is Si(CH$_3$)$_3$ or Si(CH$_3$)$_2$CH(CH$_3$)$_2$.

8. The compound of claim 5 wherein R$^3$ is Si(CH$_3$)$_3$ or Si(CH$_3$)$_2$CH(CH$_3$)$_2$.

9. The compound of claim 1 wherein R$^8$ is selected from the group consisting of C$_1$-C$_8$alkyl, C$_2$-C$_8$alkenyl, and halogen-C$_1$-C$_8$alkyl.

10. The compound of claim 1 wherein R$^8$ is heterocyclyl or heteroaryl which is unsubstituted or substituted by one or two groups independently selected from C$_1$-C$_8$alkyl, C$_1$-C$_8$alkoxy, halogen-C$_1$-C$_8$alkyl, halogen-C$_1$-C$_8$alkoxy and halogen.

11. The compound of claim 1 wherein R$^8$ is —OR$^{12}$, and R$^{12}$ is C$_1$-C$_8$alkyl or phenyl which is unsubstituted or substituted by one or two groups independently selected from C$_1$-C$_8$alkyl, C$_1$-C$_8$alkoxy, halogen-C$_1$-C$_8$alkyl, halogen-C$_1$-C$_8$alkoxy and halogen.

12. The compound of claim 1 wherein R$^8$ is —NR$^{13}$R$^{14}$, wherein R$^{13}$ and R$^{14}$ independently from each other are selected from hydrogen, C$_1$-C$_8$alkyl, and phenyl which is unsubstituted or substituted by one or two groups independently selected from C$_1$-C$_8$alkyl, C$_1$-C$_8$alkoxy, halogen-C$_1$-C$_8$alkyl, halogen-C$_1$-C$_8$alkoxy and halogen.

13. The compound of claim 1 wherein R$^8$ is C(O)—OR$^{15}$, wherein R$^{15}$ is hydrogen or C$_1$-C$_8$alkyl.

14. The compound of claim 1 wherein R$^8$ is R$^8$ is phenyl which is unsubstituted or substituted by one or two groups independently selected from C$_1$-C$_8$alkyl, C$_1$-C$_8$alkoxy, halogen-C$_1$-C$_8$alkyl, halogen-C$_1$-C$_8$alkoxy and halogen.

15. A process for the manufacture of compounds of formula I according to claim 1 which process comprises
a) reacting an acid of the formula II

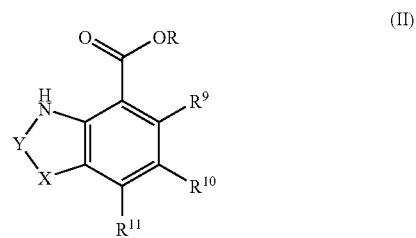

wherein —X—Y—, $R^9$, $R^{10}$ and $R^{11}$ are as defined in claim 1 and R is hydrogen or $C_1$-$C_8$alkyl, with an amine of formula III

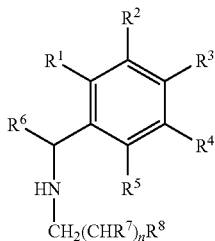
(III)

wherein $R^1$ to $R^8$ and n are as defined in claim 1, in the presence of a coupling agent;

or, alternatively, b) reacting a halogen derivative of formula IV

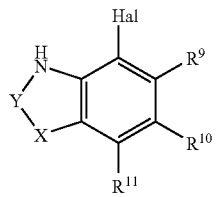
(IV)

wherein —X—Y—, $R^9$, $R^{10}$ and $R^{11}$ are as defined in claim 1 and Hal means halogen, with an amine of formula III in the presence of a suitable catalyst and carbon monoxide, and if desired, converting the compound obtained into a pharmaceutically acceptable acid addition salt.

16. A pharmaceutical composition comprising a compound according to claim 1 and a pharmaceutically acceptable carrier or adjuvant or mixture thereof.

* * * * *